United States Patent
Knight et al.

(10) Patent No.: US 9,114,398 B2
(45) Date of Patent: Aug. 25, 2015

(54) DEVICE AND METHOD FOR DIGITAL MULTIPLEX PCR ASSAYS

(75) Inventors: Ivor T. Knight, Arlington, VA (US); Hiroshi Inoue, Bethesda, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 11/947,227

(22) Filed: Nov. 29, 2007

(65) Prior Publication Data

US 2009/0143233 A1 Jun. 4, 2009

Related U.S. Application Data

(60) Provisional application No. 60/867,459, filed on Nov. 29, 2006.

(51) Int. Cl.

| | |
|---|---|
| C12Q 1/68 | (2006.01) |
| C12P 19/34 | (2006.01) |
| B01L 7/00 | (2006.01) |
| B01L 3/00 | (2006.01) |
| G01N 21/64 | (2006.01) |
| G06F 19/22 | (2011.01) |
| G01N 21/03 | (2006.01) |
| G01N 21/05 | (2006.01) |

(52) U.S. Cl.
CPC ............. *B01L 7/52* (2013.01); *B01L 3/5027* (2013.01); *C12Q 1/686* (2013.01); *G01N 21/6452* (2013.01); *G01N 21/6456* (2013.01); *G06F 19/22* (2013.01); *B01L 2200/147* (2013.01); *B01L 2300/0864* (2013.01); *G01N 21/0332* (2013.01); *G01N 21/05* (2013.01); *G01N 2021/0346* (2013.01)

(58) Field of Classification Search
CPC ............. C12Q 1/686; C12Q 2561/113; C12Q 2565/629; B01L 2200/147; B01L 2300/0864; B01L 3/5027; B01L 7/52

See application file for complete search history.

(56) References Cited

U.S. PATENT DOCUMENTS

| | | | |
|---|---|---|---|
| 5,985,651 A | 11/1999 | Hunicke-Smith | |
| 6,132,996 A | 10/2000 | Hunicke-Smith | |
| 6,140,054 A | 10/2000 | Wittwer et al. | |
| 6,156,178 A | 12/2000 | Mansfield et al. | |
| 6,174,670 B1 | 1/2001 | Wittwer et al. | |
| 6,303,343 B1 | 10/2001 | Kopf-Sill | |
| 6,379,929 B1 | 4/2002 | Burns et al. | |
| 6,472,156 B1 | 10/2002 | Wittwer et al. | |
| 6,524,456 B1 | 2/2003 | Ramsey et al. | |
| 6,524,830 B2 | 2/2003 | Kopf-Sill | |
| 6,533,912 B2 | 3/2003 | Mansfield et al. | |
| 6,569,627 B2 | 5/2003 | Wittwer et al. | |
| 6,605,454 B2 | 8/2003 | Barenburg et al. | |
| 6,660,234 B2 | 12/2003 | Stryer et al. | |
| 6,685,809 B1 | 2/2004 | Jacobson et al. | |
| 6,753,141 B2 | 6/2004 | Bernard et al. | |
| 6,833,242 B2 | 12/2004 | Quake et al. | |
| 6,852,287 B2 | 2/2005 | Ganesan | |
| 6,872,521 B1 | 3/2005 | Boyce-Jacino et al. | |
| 6,960,437 B2 | 11/2005 | Enzelberger et al. | |
| 6,977,145 B2 | 12/2005 | Fouillet et al. | |
| 7,010,391 B2 | 3/2006 | Handique et al. | |
| 7,015,030 B1 | 3/2006 | Fouillet et al. | |
| 7,027,683 B2 | 4/2006 | O'Connor et al. | |
| 7,118,910 B2 | 10/2006 | Unger et al. | |
| 7,871,571 B2 * | 1/2011 | Parker et al. | ............... 422/82.01 |
| 2002/0008308 A1 | 1/2002 | Crane, Jr. et al. | |
| 2002/0034748 A1 | 3/2002 | Quake et al. | |
| 2002/0037499 A1 | 3/2002 | Quake et al. | |
| 2002/0055149 A1 | 5/2002 | Kopf-Sill | |
| 2002/0068357 A1 | 6/2002 | Mathies et al. | |
| 2002/0187564 A1 | 12/2002 | Chow et al. | |
| 2002/0197630 A1 | 12/2002 | Knapp et al. | |
| 2003/0204331 A1 * | 10/2003 | Whitney et al. | .................. 702/32 |
| 2003/0224434 A1 | 12/2003 | Wittwer et al. | |
| 2004/0005720 A1 | 1/2004 | Cremer et al. | |
| 2004/0007463 A1 | 1/2004 | Ramsey et al. | |
| 2004/0224325 A1 | 11/2004 | Knapp et al. | |
| 2005/0009051 A1 | 1/2005 | Han et al. | |
| 2005/0019902 A1 | 1/2005 | Mathies et al. | |

(Continued)

FOREIGN PATENT DOCUMENTS

| | | |
|---|---|---|
| DE | 10324912 A1 | 1/2005 |
| WO | 2008005321 A2 | 1/2008 |

OTHER PUBLICATIONS

Pohl et al., "Principle and Applications of digital PCR," Expert Rev. Mol. Diagn. 4(1):41-47 (2004).

Hunter, "Margin of Error and Confidence Levels Made Simple." Published online Nov. 23, 2006. Retrieved from the Internet Dec. 11, 2008 at <<URL: http://web.archive.org/web/20061123170226/http://www.isixsigma.com/library/content/c040607a.asp>> 2 pages.

Chamberlain, et al., "Deletion Screening of the Duchenne Muscular Dystrophy Locus Via Multiplex DNA Amplification," Nucleic Acids Research Special Publicaiton, vol. 16, No. 23, pp. 11141-11156 (Jan. 1, 1988).

(Continued)

*Primary Examiner* — Young J Kim

(74) *Attorney, Agent, or Firm* — Rothwell, Figg, Ernst & Manbeck, P.C.

(57) ABSTRACT

A method and device for digital multiplex PCR assays employ a microfluidic chip for performing real-time, continuous flow PCR within microchannels of the chip. A stream of sample material is introduced into each microchannel and alternating boluses of assay-specific reagents and buffer are introduced into the stream to form sequentially configured test boluses. A PCR procedure is performed on the test boluses followed by a thermal melt procedure. During the thermal melt procedure, fluorescent output is detected and fluorescence vs temperature data is collected and compared to expected normal correlations. The results, positive or negative, are converted to digital format, with positive results designated as "1" and negative results designated as "0", or vice versa.

26 Claims, 5 Drawing Sheets

(56) References Cited

U.S. PATENT DOCUMENTS

| | | | |
|---|---|---|---|
| 2005/0064465 A1 | 3/2005 | Dettloff et al. |
| 2005/0089894 A1 | 4/2005 | Ginns et al. |
| 2005/0098435 A1 | 5/2005 | Jacobson et al. |
| 2005/0136448 A1 | 6/2005 | Hartel et al. |
| 2005/0147977 A1 | 7/2005 | Koo et al. |
| 2005/0147979 A1 | 7/2005 | Koo et al. |
| 2005/0202468 A1 | 9/2005 | Koo et al. |
| 2005/0202470 A1 | 9/2005 | Sundberg et al. |
| 2005/0202489 A1 | 9/2005 | Cho et al. |
| 2005/0221373 A1 | 10/2005 | Enzelberger et al. |
| 2005/0233335 A1 | 10/2005 | Wittwer et al. |
| 2005/0282224 A1 | 12/2005 | Fouillet et al. |
| 2006/0004526 A1 | 1/2006 | Hadd et al. |
| 2006/0011478 A1 | 1/2006 | Fouillet et al. |
| 2006/0051807 A1 | 3/2006 | Fuller |
| 2006/0062696 A1 | 3/2006 | Chow et al. |
| 2006/0134644 A1 | 6/2006 | Hartel et al. |
| 2006/0169588 A1 | 8/2006 | Jacobson et al. |
| 2006/0194218 A1 | 8/2006 | Cook et al. |
| 2006/0246495 A1 | 11/2006 | Garrett et al. |
| 2006/0257893 A1 | 11/2006 | Takahashi et al. |
| 2006/0286599 A1 | 12/2006 | Gierde et al. |
| 2007/0026421 A1 | 2/2007 | Sundberg et al. |
| 2007/0037182 A1 | 2/2007 | Gaskin et al. |
| 2007/0065844 A1 | 3/2007 | Golub et al. |
| 2007/0231799 A1 | 10/2007 | Knight et al. |
| 2007/0264630 A1 | 11/2007 | Gumbrecht et al. |

OTHER PUBLICATIONS

Varga, et al., "Detection and differentiation of *Plum pox virus* using real-time multiplex PCR with SYBR Green and melting curve analysis: a rapid method for strain typing," Journal of Virological Methods, vol. 123, No. 2, pp. 213-220 (Feb. 1, 2005).

Elenitoba-Johnson, et al., "Multiplex PCR by multicolor fluorimetry and fluorescence melting curve analysis," Nature Medicine, vol. 7, No. 2, pp. 249-253 (2001).

Sundberg, et al., "Solution-phase DNA mutation scanning and SNP genotyping by nanoliter melting analysis," Biomed Microdevices, vol. 9, pp. 159-166 (2007).

Y. Nagaoka, "Flows in Microdevices," Nagare, 2002, vol. 21, p. 419-428.

* cited by examiner

| | H | G | H | G | F | E | D | F | E | D | C | B | A | C | B | A |
|---|---|---|---|---|---|---|---|---|---|---|---|---|---|---|---|---|
| 1 CONTROL | 1 | 1 | 1 | 1 | 1 | 1 | 1 | 1 | 1 | 1 | 1 | 1 | 1 | 1 | 1 | 1 |
| 0 CONTROL | 0 | 0 | 0 | 0 | 0 | 0 | 0 | 0 | 0 | 0 | 0 | 0 | 0 | 0 | 0 | 0 |
| | 0 | 1 | 0 | 1 | 0 | 1 | 1 | 0 | 1 | 1 | 0 | 0 | 1 | 0 | 0 | 1 |
| | 0 | 0 | 0 | 0 | 0 | 1 | 1 | 0 | 1 | 1 | 1 | 1 | 1 | 1 | 1 | 1 |
| | 1 | 1 | 1 | 1 | 1 | 0 | 1 | 0 | 0 | 1 | 0 | 1 | 1 | 0 | 1 | 1 |
| | 0 | 1 | 0 | 1 | 1 | 1 | 1 | 1 | 1 | 1 | 0 | 1 | 0 | 0 | 1 | 0 |
| | 1 | 1 | 1 | 1 | 0 | 0 | 0 | 0 | 0 | 0 | 1 | 0 | 0 | 1 | 0 | 0 |
| | 0 | 0 | 0 | 0 | 1 | 1 | 1 | 1 | 1 | 1 | 0 | 1 | 1 | 0 | 1 | 1 |
| | 1 | 1 | 1 | 1 | 0 | 0 | 0 | 0 | 0 | 0 | 1 | 0 | 0 | 1 | 0 | 0 |
| | 0 | 1 | 0 | 1 | 0 | 1 | 1 | 0 | 1 | 1 | 0 | 0 | 1 | 0 | 0 | 1 |
| | 1 | 1 | 1 | 1 | 1 | 0 | 1 | 0 | 0 | 1 | 0 | 1 | 1 | 0 | 1 | 1 |
| | 0 | 1 | 0 | 1 | 1 | 1 | 1 | 1 | 1 | 1 | 0 | 1 | 0 | 0 | 1 | 0 |
| | 0 | 0 | 0 | 0 | 0 | 1 | 1 | 0 | 1 | 1 | 1 | 1 | 1 | 1 | 1 | 1 |
| | 1 | 1 | 1 | 1 | 1 | 0 | 1 | 0 | 0 | 1 | 0 | 1 | 1 | 0 | 1 | 1 |
| | 0 | 1 | 0 | 1 | 1 | 1 | 1 | 1 | 1 | 1 | 0 | 1 | 0 | 0 | 1 | 0 |
| | 1 | 1 | 1 | 1 | 0 | 0 | 0 | 0 | 0 | 0 | 1 | 0 | 0 | 1 | 0 | 0 |
| | 0 | 1 | 0 | 1 | 0 | 1 | 1 | 0 | 1 | 1 | 0 | 0 | 1 | 0 | 0 | 1 |
| | 1 | 0 | 1 | 0 | 1 | 1 | 1 | 1 | 1 | 1 | 1 | 0 | 1 | 1 | 0 | 1 |
| | 1 | 1 | 1 | 1 | 0 | 0 | 0 | 0 | 0 | 0 | 1 | 0 | 0 | 1 | 0 | 0 |
| | 0 | 0 | 0 | 0 | 1 | 1 | 1 | 1 | 1 | 1 | 0 | 1 | 1 | 0 | 1 | 1 |
| | 1 | 1 | 1 | 1 | 0 | 0 | 0 | 0 | 0 | 0 | 1 | 0 | 0 | 1 | 0 | 0 |
| | 1 | 1 | 1 | 1 | 1 | 0 | 1 | 0 | 0 | 1 | 0 | 1 | 1 | 0 | 1 | 1 |
| | 0 | 1 | 0 | 1 | 1 | 1 | 1 | 1 | 1 | 1 | 0 | 1 | 0 | 0 | 1 | 0 |
| | 0 | 1 | 0 | 1 | 0 | 1 | 1 | 0 | 1 | 1 | 0 | 0 | 1 | 0 | 0 | 1 |
| | 1 | 0 | 1 | 0 | 1 | 1 | 1 | 1 | 1 | 1 | 1 | 0 | 1 | 1 | 0 | 1 |
| | 1 | 1 | 1 | 1 | 0 | 0 | 0 | 0 | 0 | 0 | 1 | 0 | 0 | 1 | 0 | 0 |
| | 0 | 0 | 0 | 0 | 1 | 1 | 1 | 1 | 1 | 1 | 0 | 1 | 1 | 0 | 1 | 1 |
| | 0 | 1 | 0 | 1 | 1 | 1 | 1 | 1 | 1 | 1 | 0 | 1 | 0 | 0 | 1 | 0 |
| | 1 | 1 | 1 | 1 | 0 | 0 | 0 | 0 | 0 | 0 | 1 | 0 | 0 | 1 | 0 | 0 |
| | 0 | 0 | 0 | 0 | 0 | 1 | 1 | 0 | 1 | 1 | 1 | 1 | 1 | 1 | 1 | 1 |
| | 1 | 1 | 1 | 1 | 1 | 0 | 1 | 0 | 0 | 1 | 0 | 1 | 1 | 0 | 1 | 1 |
| | 0 | 1 | 0 | 1 | 0 | 1 | 1 | 0 | 1 | 1 | 0 | 0 | 1 | 0 | 0 | 1 |

FIG. 4

SEQUENCE LISTING

<160> NUMBER OF SEQ ID NOS: 4

<210> SEQ ID NO 1
<211> LENGTH: 11
<212> TYPE: DNA

-continued

```
<213> ORGANISM: Homo sapiens

<400> SEQUENCE: 1
tcctgaggag a                                                          11

<210> SEQ ID NO 2
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Complementary strand to SEQ ID NO: 1

<400> SEQUENCE: 2
tctcctcagg a                                                          11

<210> SEQ ID NO 3
<211> LENGTH: 11
<212> TYPE: DNA
<213> ORGANISM: Homo sapiens

<400> SEQUENCE: 3
tcctgtggag a                                                          11

<210> SEQ ID NO 4
<211> LENGTH: 11
<212> TYPE: DNA
<213> ORGANISM: Homo sapiens
<220> FEATURE:
<221> NAME/KEY: misc_feature
<222> LOCATION: (1)..(11)
<223> OTHER INFORMATION: Complementary strand to SEQ ID NO: 3

<400> SEQUENCE: 4
tctccacagg a                                                          11
```

DEVICE AND METHOD FOR DIGITAL MULTIPLEX PCR ASSAYS

This application claims the benefit of Provisional Patent Application Ser. No. 60/867,459, filed on Nov. 29, 2006, which is incorporated herein by reference.

BACKGROUND OF THE INVENTION

1. Field of the Invention

The present invention relates to processes employing continuous flow multiplex assays and, more specifically, processes employing continuous flow multiplex assays in which results are converted to digital format. Multiple assays can be run on each of multiple patient samples, thereby permitting high levels of multiplexing and flexibility.

2. Discussion of the Related Art

Currently, multiplex polymerase chain reaction ("PCR") assays are carried out in a static format, where each reaction is completed in a separate tube, capillary or well of a multi-well plate. In all cases, the number of PCR reactions that can be performed is limited by the number of locations in the fixed format. Most commonly, a 96-well format is utilized which would allow, for example, one patient DNA sample to be tested with up to 96 different PCR assays. In this format, the number of patient DNA samples to be tested could be increased, but at the cost of reducing the number of different PCR assays that could be run. For example, in the 96-well format, 24 different patient DNA samples could be tested, with only 4 PCR assays. More recently a 384-well plate format has been introduced, which increases the number of patient-assay combinations that can be run, but even this format would not accommodate more that 3 patient DNA samples if 100 different PCR assays were needed.

DNA microarrays that permit interrogation of thousands of genetic loci are an alternative to the limitations of plate-based assays, but the key disadvantages are limitations on reliability of the output data, the high expense and long time required for such assays, as well as the fact that a microarray is a fixed format that does not permit the end-user to change assays as necessary.

Many new diagnostic PCR assays are directed to identifying single nucleotide polymorphisms (SNPs) that diagnose the disease status of the patient, diagnose a risk for developing the disease or predict a patient's response to various therapeutic drugs. In most cases, multiple SNP determinations are necessary for accurate diagnosis or predictions of therapy response. The advent of efforts to map all SNPs in the human genome is increasing the number of SNPs that are associated with a particular disease state or therapeutic outcome. Multiplex analyses, with tens of assays being performed at once, are currently required for many diagnostic and therapy prediction applications. There is currently an unmet demand for PCR assay formats that permit high multiplexing and a flexible format to accommodate new targets as needed.

Thermal melting analysis is currently used in the art to distinguish SNPs in PCR-based assays. Wittwer has disclosed methods and devices that utilize fluorescent molecules to determine the thermal melting profile of nucleic acids and distinguish SNPs based on thermal melting profiles (See U.S. Pat. Nos. 6,174,670; 6,140,054; 6,472,156; 6,753,141; 6,569,627 and United States Patent Application Publication Nos. 2003-0224434A1 and 2005-0233335A1). These methods and devices, however, suffer from the same limitations described above.

SUMMARY OF THE INVENTION

The invention described herein enables thermal melting analysis to be used for SNP detection in a continuous flow PCR microfluidic chip, producing a digital output from multiplex testing.

The continuous flow format permits individual PCR reactions and thermal melts of a multiplex PCR plus Thermal Melt assay to be monitored individually and separately, without the influence of other PCR reactions and thermal melts in the multiplex assay. The continuous flow format permits a higher degree of multiplexing than in the 96 and 384 well formats, necessary for complex pharmocogenetic assays. The continuous flow format is more flexible than static, fixed formats. Moreover, the user can define the number of assays to use and the order in which they are conducted. The digital output (e.g., designating positive results as "1" and negative results as "0" or vice versa) simplifies interpretation of results and permits easy transfer of the data to digital media.

Aspects of the invention are embodied in a method for performing multiple assays on multiple samples with a microfluidic chip comprising multiple reaction channels. The method includes the steps of providing a continuous flow of sample within each of a plurality of the reaction channels and alternately introducing an amount of reagent material and buffer material into each of the channels to form, along a portion of the length of each channel, a continuous flow comprising boluses of test solution sequentially alternating with carrier fluid. The test solution comprises a mixture of sample and reagent material, and the carrier fluid comprises a mixture of sample and buffer material. An amplification procedure is performed on the continuous flow within each channel, and then a signal emitted by each bolus of test material is detected after performing the amplification procedure. The detected signal is analyzed to ascertain the presence or absence of a nucleotide of interest within the bolus of sample material. The results of the analyzing step are converted to a digital format by designating the result as a 1 or 0, wherein a result indicating the presence of the nucleotide of interest is designated as a 1 and a result indicating the absence of the nucleotide of interest is designated as a 0, or vice versa.

Aspects of the invention are embodied in a system for performing the process described above includes a microfluidic chip comprising a plurality of reaction channels, a sample well and a waste well on opposite ends of each reaction channel, a sipper, and a network of channels emanating from the sipper and connecting the sipper to each of said plurality of reaction channels and configured to divide substance drawn by the sipper among each of the reaction channels. The system further includes a temperature control system configured to thermocycle the test solution along a defined section of each channel for performing real-time PCR in the test solution and an optical imaging system integral with or proximal to the microfluidic chip and configured to illuminate each channel and to detect a fluorescent signal at a plurality of locations along each channel. The system further includes a controller programmed to cause the system to perform digital, multiplex PCR assays.

Other aspects of the present invention, including the methods of operation and the function and interrelation of the elements of structure and functional elements, will become more apparent upon consideration of the following description and the appended claims, with reference to the accompanying drawings, all of which form a part of this disclosure, wherein like reference numerals designate corresponding parts in the various figures.

BRIEF DESCRIPTION OF THE DRAWINGS

FIG. 4 is a table showing an array of assay results for eight multiplex assays (each performed twice) performed on 30 patient DNA samples and two controls.

DETAILED DESCRIPTION OF THE INVENTION

Unless defined otherwise, all technical and scientific terms used herein have the same meaning as commonly understood by one of ordinary skill in the art to which the invention pertains. Although any methods and materials similar or equivalent to those described herein can be used in the practice of the present invention, the preferred materials and methods are described herein.

Figure 1:
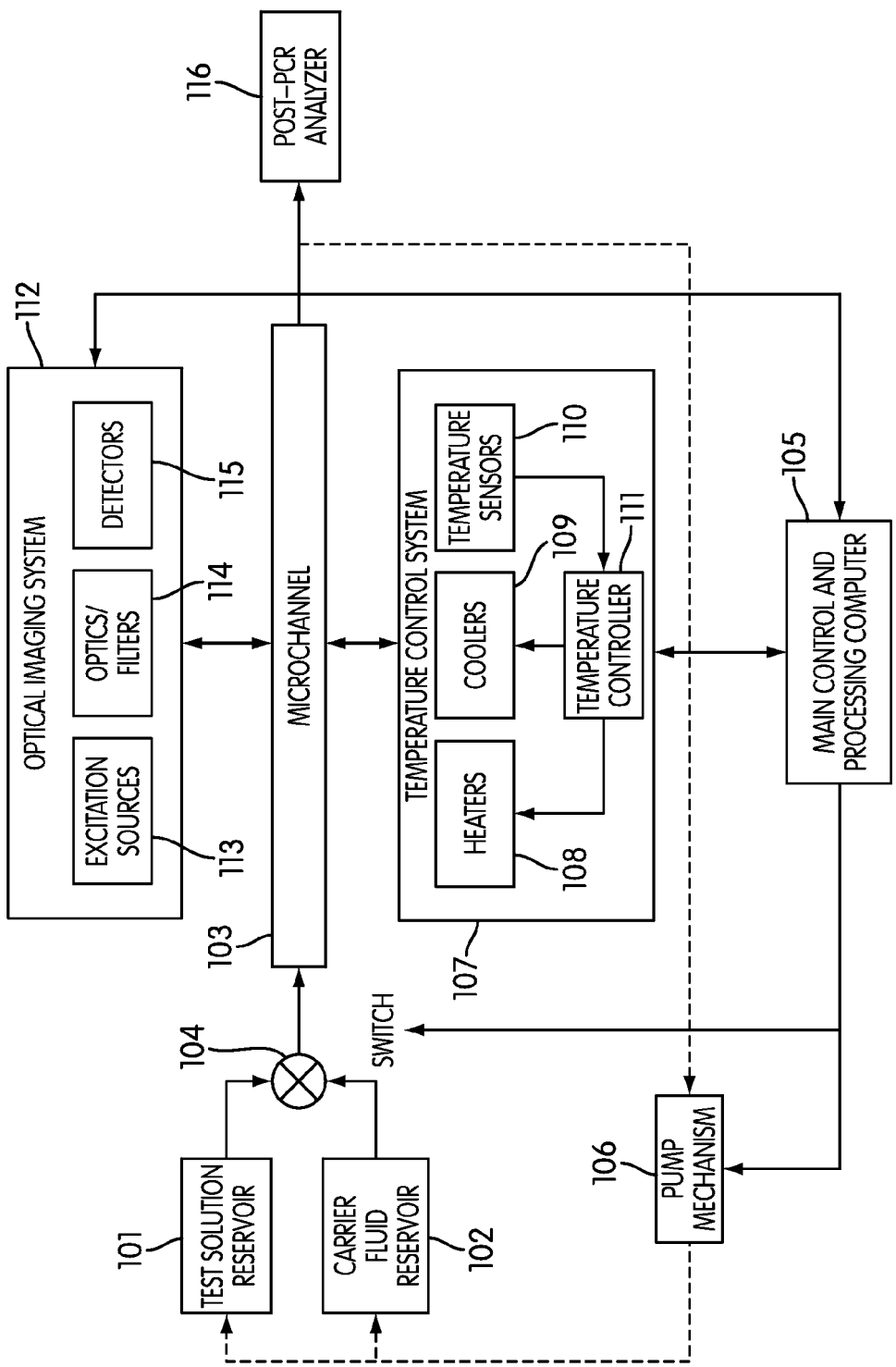
FIG. 1 is block diagram of a real-time PCR architecture with which the present invention may be implemented.

FIG. 1 illustrates a block diagram of a real-time PCR architecture with which the present invention may be implemented. The system includes a test solution reservoir 101, which may be a reservoir containing multiple test solutions, e.g., test samples. The system further includes a carrier fluid reservoir 102. The test fluid reservoir and/or the carrier fluid reservoir may comprise chambers within a cartridge that is coupled to the microfluidic device, such as the cartridge described in commonly-assigned U.S. patent application Ser. No. 11/850,229, the disclosure of which is hereby incorporated by reference. The test solution may be substantially the same as the carrier fluid, except that the test solution comprises all the necessary real-time PCR reagents. The real-time PCR reagent mixture may include PCR primers, dNTPs, polymerase enzymes, salts, buffers, surface-passivating agents, and the like. In addition, the real-time PCR mixture may include a non-specific fluorescent DNA detecting molecule, a sequence-specific fluorescent DNA probe, or a marker. The carrier fluid may be an immiscible fluid (such as an oil, a fluorinated liquid, or any other nonaqueous or hydrophobic solvent). The purpose of the carrier fluid is to deter transfer of material from one test bolus to another. Another purpose of the carrier fluid is to provide a distinguishable transition between boluses that may be used to track the fluid flow in the channel. The carrier fluid may include a marker.

Figure 2:
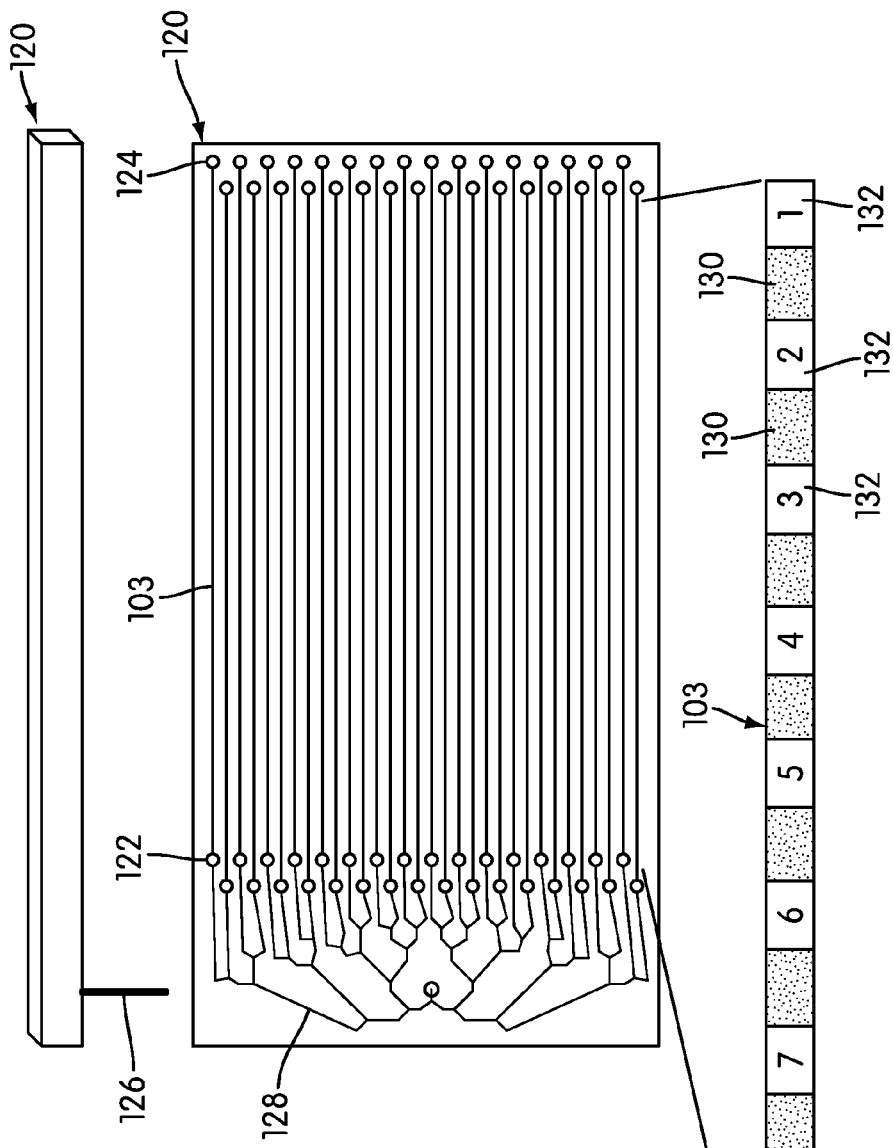
FIG. 2(A) is a side view of a microfluidic chip with which the present invention may be implemented.
FIG. 2(B) is a top view of the microfluidic chip of FIG. 2(A)
FIG. 2(C) is an enlarged view of a microfluidic channel of the microfluidic chip of FIG. 2(B)

The test solution and carrier fluid are introduced into a microchannel 103, for example, through a switch 104. The dimensions of the microchannel are small enough to allow for the amplification and detection of a single DNA molecule originally present in the test solution. In the present invention, microchannel 103 is one of several microchannels that are part of a microfluidic device (such as shown in FIG. 2). Switch 104 is under control of a main control and processing computer 105 such that the carrier fluid and the test solution are sequentially alternately introduced into microchannel 103. The volume of the test solution and carrier fluid that is introduced into microchannel 103 is selected such that there is minimal blending between them during movement through microchannel 103.

Alternatively, sample material may be provided as a continuous stream in the microchannel 103, and assay-specific reagents and buffer material may be alternately introduced into the continuous stream of sample material via a sipper, as described in more detail below.

A multitude of reactions in series (or sequential reactions) can thus be carried out in the same microchannel 103 as a result of the continuous movement of different test solutions through microchannel 103, each separated by the carrier fluid. Where, as in the present invention, microchannel 103 is one of several microchannels in a microfluidic device, then a multitude of reactions can also be carried out in parallel in the microchannels of the microfluidic device. The flow rate of the carrier fluid and test solution through microchannel 103 is controlled by pump mechanism 106. Pump mechanism 106 is under control of main control and processing computer 105 in order to regulate the flow rate of the test solution and the carrier fluid in microchannel 103. The flow rate is regulated such that a desired number of PCR cycles are performed as the test solution passes through microchannel 103.

Pump mechanism 106 can regulate the flow rate of the test solution and carrier fluid by positive pressure at the upstream side or inlet of microchannel 103 or by negative pressure at the downstream side or outlet of microchannel 103. In one embodiment, the pressure difference is approximately 1 psi, although other pressure differences may be utilized. The length of microchannel 103 is suitable for the completion of the desired number of PCR cycles such as, for example, 10 to 50 cycles of PCR, or any number in between, as the test solution moves through the reaction zone of microchannel 103. The reaction zone of microchannel 103 is the region of the microchannel in which the temperature is cycled for conducting the PCR cycles. Typically, 25-30, 25-35, 25-40, 30-35, 30-40 or 35-40 PCR cycles are performed for standard amplification reactions. The length of microchannel 103 to accomplish the desired number of PCR cycles is also dependent on the volume of test solution and carrier fluid that are sequentially alternately moved through microchannel 103. For example, if the reaction zone is 40 mm, then the minimum volume of test solution would occupy 1 mm in the reaction zone of microchannel 103, and the maximum volume of test solution would occupy 20 mm in the reaction zone of microchannel 103. Thus, in this non-limiting example, a minimum of 1 sample and a maximum of 20 samples could be amplified as the test solution moves through the reaction zone of microchannel 103. Of course, the microchannel length and sample volumes can be selected to amplify any number of samples.

A temperature control system 107 is included in the system to control and cycle the temperature to produce suitable temperatures for the PCR cycles as the test solution moves through microchannel 103. Suitable temperatures for the PCR cycles are well known to skilled artisan and may include a first temperature in the range of about 85° C. to about 100° C., a second temperature in the range of about 20° C. to about 70° C., and a third temperature in the range of about 55° C. to about 80° C. Temperature control system 107 is integral with or proximal to microchannel 103 or to the microchannels of a microfluidic device. Temperature control system 107 includes heaters 108, coolers 109, temperature sensors 110 and a temperature controller 111. Temperature controller 111 collects temperature information from the temperature sensors 110 and generates control signals based on the temperature information. The control signals are sent to the heaters 108 or coolers 109 to cycle the temperature in microchannel 103 for the desired PCR cycles. Temperature controller 111 is under control of main control and processing computer 105 so that the temperature is cycled such that the desired number of PCR cycles is performed as the test solution moves through microchannel 103. The different PCR reactions in the different test solutions follow one after another in microchannel 103 in a serial manner due to the continuous flow in microchannel 103.

Heating and cooling of the microchannel 103 may be accomplished by blowing air of the appropriate temperatures. Alternatively, the heating and cooling may be accomplished by circulating water or fluid baths or by Peltier-effect elements which are well known to the skilled artisan. Junctions of different metals, which are crossed by an electric current, make it possible to cool or heat a small surface. A temperature probe on the Peltier element makes it possible to regulate the power, which is proportional to the electrical intensity, and thus makes it possible to regulate the temperature. A metal block may be used as a thermal transfer element and includes a thermoelectric cooler in contact with the metal block. This metal block can be made of any metal (or metal alloy) having suitable thermal transfer properties such as, for example, aluminum. In order to reduce backscatter of light from the metal block it is preferably painted black or anodized. The temperatures for the PCR cycles can equilibrate at suitable time intervals for this thermal transfer unit. For example, the temperatures for the PCR cycles can equilibrate within approximately 1-2 seconds or even faster.

Temperature control system 107 preferably cycles the temperature in an entire defined section of microchannel 103, i.e., that section of microchannel 103 in which the PCR cycles are performed. This defined section of microchannel 103 is also known as the reaction zone. Thus, a constant temperature zone is used to provide the thermal cycling. An appropriately programmed computer controls the temperature cycling of the thermal transfer element. Moreover, heating and cooling are applied to a length of the channel (the reaction zone) such that its temperature follows a PCR profile in time. The test boluses are pumped through this reaction zone at a flow rate (speed) such that the number of PCR cycles required is achieved during the time the bolus flows from the upstream end to the downstream end of the reaction zone.

Alternatively, temperature control system 107 applies spatial temperature zones along microchannel 103 to achieve a polymerase chain reaction. In one aspect, the temperature is cycled using a thermal transfer element along portions of the microchannel 103 or the microchannels of a microfluidic device. In another aspect, the thermal transfer element cycles the temperature in portions of microchannel 103. An appropriately programmed computer controls the temperature cycling of the thermal transfer element. In accordance with this embodiment, heating and cooling are applied to portions of the channel such that a PCR temperature profile is followed. The test boluses are pumped through this reaction zone at a flow rate (speed) such that the number of PCR cycles required is achieved during the time the bolus flows from the upstream end to the downstream end of the reaction zone.

An optical imaging system 112 detects emissions (e.g., fluorescence or chemiluminescence) which are indicative of the presence—and possibly the amount—of an SNP or other nucleic acid of interest (i.e., amplification products) and to monitor the flow rate of the test solution in microchannel 103. In one embodiment, the optical imaging system 112 is a fluorescent imaging system that preferably includes one or more excitation sources 113, one or more optics/filters 114 and one or more detectors 115. The excitation sources 113 generate light at desired wavelengths to excite the labels used for detecting the amplification products during real-time PCR and/or to detect markers that may be present to monitor the flow rate of the test solution in microchannel 103. Optics/filters 114 are used to form a beam of light and/or to direct the light from excitation sources 113 to the appropriate positions on the microchannel 103. Optics/filters 114 are also used to filter the light to exclude light of undesired wavelengths or to reduce backscatter from reaching detectors 115. The desired wavelengths to excite the labels used in real-time PCR will depend on the precise labels and/or markers used, e.g., intercalating dyes, molecular beacons, quantum dots or TaqMan® probes, which wavelengths are well known to skilled artisans. Similarly, the emission wavelengths of the precise labels and/or markers are well known to skilled artisans. Detectors 115 detect the emission wavelengths of the excited labels and/or markers and measure the intensity of the emitted light. Optical imaging system 112 preferably is able to distinguish between multiple microchannels in a microfluidic device.

Optical imaging system 112 is under control of main control and processing computer 105 which directs the optical/fluorescence imaging system 112 to measure the intensity of the emitted light at desired time intervals, such as, for example, at least once during each PCR cycle at a plurality of locations in microchannel 103 or in the microchannels of a microfluidic device. Detectors 115 generate a signal or an image of the intensity of the emitted light and direct it to main control and processing computer 105 for analysis of the amplification product and for monitoring the flow rate of the test solution. Detectors 115 may include multiple-pixel array detectors (such as a CCD detector) and/or discrete single-pixel or non-imaging detectors. Detectors 115 may be integral with or proximal to microchannel 103 or to the microchannels of a microfluidic device. Detectors 115 may be stationary or may be scanning. The detectors 115 should have appropriate resolution for obtaining meaningful results and for monitoring of fluid flow in microchannel 103, particularly because the fluid is continuously moving in microchannel 103.

As described above, the real-time PCR mixture may include a non-specific fluorescent DNA detecting molecule (such as an intercalating dye), a sequence-specific fluorescent DNA probe (such as a molecular beacon, a TaqMan® probe or a quantum dot probe), or a flow marker (such as a quantum dot), and the carrier fluid may include a flow marker. In one embodiment, the optical imaging system 112 is utilized to detect the intensity of the fluorescence from the DNA detecting molecule or the probe (i.e., the intensity of the fluorescent signal) and/or to detect the fluorescence of the marker. The fluorescence of the marker can be used to delineate the test solution from the carrier fluid and can also be used to determine and monitor the flow speed of the test solution or carrier fluid. The intensity of the fluorescent signal can be used to detect amplified product, to determine the quantity of amplified product, to determine the number of original molecules present in the test solution, and the like as well known to a skilled artisan for real-time PCR. The intensity of the fluorescent signal can also be used to determine and monitor the flow speed of the test solution.

The intensity of the fluorescent signal may be measured (e.g., an image of the fluorescent signal is taken) at a specific time and/or temperature during the PCR temperature cycle.

Alternatively, the intensity of the fluorescent signal can be measured once during each PCR cycle. According to one aspect of the present invention, emissions can be measured during a thermal melt procedure following the PCR procedure.

The optimal time to capture the image depends on the chemistry utilized. For example, if an intercalating dye is used to detect amplified product, the image should be captured at the end of the extension phase of the PCR cycle. If a TaqMan probe is used to detect the amplified product, the image could be captured at any time during the PCR cycle. Main control and processing computer 105 can be programmed to take the image at the time and temperature desired. Optical imaging system 112 may be configured to measure the intensity of the fluorescent signal at a plurality of locations. The plurality of locations at which the intensity of the fluorescent signal is measured may be different sections of the microchannel. The plurality of locations at which the intensity of the fluorescent signal is measured may be the entire defined section (i.e., reaction zone) of the microchannel. Alternatively, an image of at least one fluorescent signal along the length of the channel is made. In a further embodiment, the image capture is performed repeatedly on consecutive temperature cycling periods. The image may be created or the intensity of the fluorescent signal measured using a multiple-pixel array detector (such as a CCD or CMOS image sensor) or a single pixel detector. Fluorescent light may be collected using large field-of-view imaging optics and/or small field-of-view optics such as a fiber-optic/lens combination. A stationary mechanism or a scanning mechanism or both may be used to capture the image. The data concerning the intensity of the fluorescent signal is processed by an appropriately programmed computer.

After test solution has moved through microchannel 103 and completed the desired number of PCR cycles, it may optionally be sent to a post-PCR analyzer 116. Post-PCR analyzer 116 may include any analytical technique that can be used on PCR amplification products. Such techniques include, but are not limited to, sequencing, electrophoresis, probing, melt curve analysis, and the like.

One example of a continuous flow PCR chip device is described in commonly-assigned U.S. patent application Ser. No. 11/850,229, "Chip and Cartridge Design Configuration for Performing Micro-Fluidic Assays", the disclosure of which is incorporated by reference. In the chip described in the '229 application, DNA samples are introduced into the top of the chip via a cartridge having sample-holding chambers, which is attached to the top of the chip. Each cartridge communicates with a sample well, making each channel a continuous stream of a single patient DNA sample. Reagents are introduced into this stream via a sipper which draws reagent from a container external to the microfluidic chip. Aspects of the current invention include an application for micro-fluidic chip configurations, such as those described in the Ser. No. 11/850,229 application, that allow multiplex PCR assays, such as pharmacogenetic assays requiring up to 100 PCR reactions, to be carried out in a continuous flow format with a separate, digital output for each PCR reaction. Another example of a continuous flow PCR chip device is described in commonly-assigned U.S. patent application Ser. No. 11/606,006, "Systems and Methods for Monitoring the Amplification and Dissociation Behavior of DNA Molecules", the disclosure of which is incorporated by reference in its entirety.

FIGS. 2(A)-(C) show a multi-channel microfluidic chip 120, which is processed within a system having, generally, the architecture shown in FIG. 1 and described above and which is configured for implementing aspects of the present invention. FIG. 2(A) shows a side view of the microfluidic chip 120, and FIG. 2(B) shows a top view of the microfluidic chip 120. FIG. 2(C) shows, in an enlarged manner, continuous flow, multiplex assays flowing through a single channel 103 of the microfluidic chip 120.

As shown in FIG. 2(B), the microfluidic chip 120 includes patient sample wells 122 at which patient sample material is introduced into the channels 103 extending from each well 122. In the illustrative embodiment shown in FIG. 2, there are thirty-two wells 122 for patient samples and thirty-two associated channels 103. The embodiment shown in FIG. 2(B) is a non-limiting example; the chip may have more than or fewer than thirty-two sample wells and associated channels.

In the illustrated embodiment, as shown in FIG. 2(A), the microfluidic chip 120 also includes a single sipper 126 for sipping up reagent cocktail (solution) for each assay (PCR primers specific for a particular SNP, double stranded binding dye, optional probe, buffer, etc.)

The microfluidic chip 120 also includes waste wells 124 at which materials are stored after the assay is complete. Alternatively, materials may be directed from waste wells 124 to an external waste compartment (not shown) after the assay is complete.

Referring to FIG. 2(C), flow within each channel 103 is from left to right, and flow terminates at the waste wells 124. Each patient DNA sample is pre-loaded into one of the thirty-two wells 122, and a continuous flow of sample material is drawn from the well 122 through the channel 103, for example, by applying a vacuum to the opposite end of the channel 103. Assay-specific reagent materials (i.e., "reagent cocktails") are sipped through sipper 126 alternately with a buffer sip by moving the sipper 126 between containers holding the desired reagent cocktail and container holding buffer solution. Each reagent cocktail and buffer sip is split several times in a network of channels 128 to dispense the same reagent cocktail and buffer solution into each channel 103 containing patient DNA. Thus, each channel contains a continuous stream of patient DNA, with specific reagent sets or "droplets" or "boluses" 132 and buffer 130 interspersed along the channel 103. Each reagent set 132 may contain different assay-specific reagents for performing a different PCR assay and identifying a different SNP, or two or more of the reagent sets 132 may contain the same assay-specific reagents.

As an alternative to the sipper, reagents and dyes can be introduced into the channels by other means, such as thermal heating (bubble jet) or a piezoelectric printing mechanism.

Thermal cycling is carried out along the length of the channel 103 by the temperature control system 107 under the control of the main control and processing computer 105, and the PCR reactions proceed within the reagent sets 132 as the stream moves along the channel 103. At the end of the channel 103, prior to entering the waste well 124, and while still moving, the temperature of each reagent droplet 132 is ramped to effect a thermal melting of the DNA within the droplet 132, while the appropriate fluorescence profile is monitored using the optical imaging system 112 under the control of the main control and processing computer 105. The data output for each droplet is the fluorescence profile as a function of temperature, which is converted to a digital signal as described below.

The PCR assays are conducted in serial along each of the channels 103, and the patient DNA samples are run in parallel across the different channels 103.

TABLE 1

| Number of Patient Samples | Total Number of Tests Performed at Each Level of Multiplexing | | | |
|---|---|---|---|---|
| | 10 SNPs | 25 SNPs | 50 SNPs | 100 SNPs |
| 10 | 100 | 250 | 500 | 1,000 |
| 20 | 200 | 500 | 1,000 | 2,000 |
| 30 | 300 | 750 | 1,500 | 3,000 |

Table 1 illustrates different possible assay multiplexing scenarios based on different numbers of patients and SNPs requiring analysis. For 10 patient samples, each requiring the identification of 10 SNPs, a total of 100 tests (PCR assays) must be run, for 10 patient samples requiring 25 SNPs, 250 tests must be run, and so on.

The exemplary chip 120 shown in FIG. 2(B) can accommodate any of the test requirements listed in Table 1. That is, chip 120 can accommodate up to thirty-two different patient samples, and the number of tests that can be performed in the reagent sets 132 arranged serially along the length of the channel 103 is limited only by the amount of sample material that is available and may be 10 to 100 or more serially arranged tests.

Figure 3:
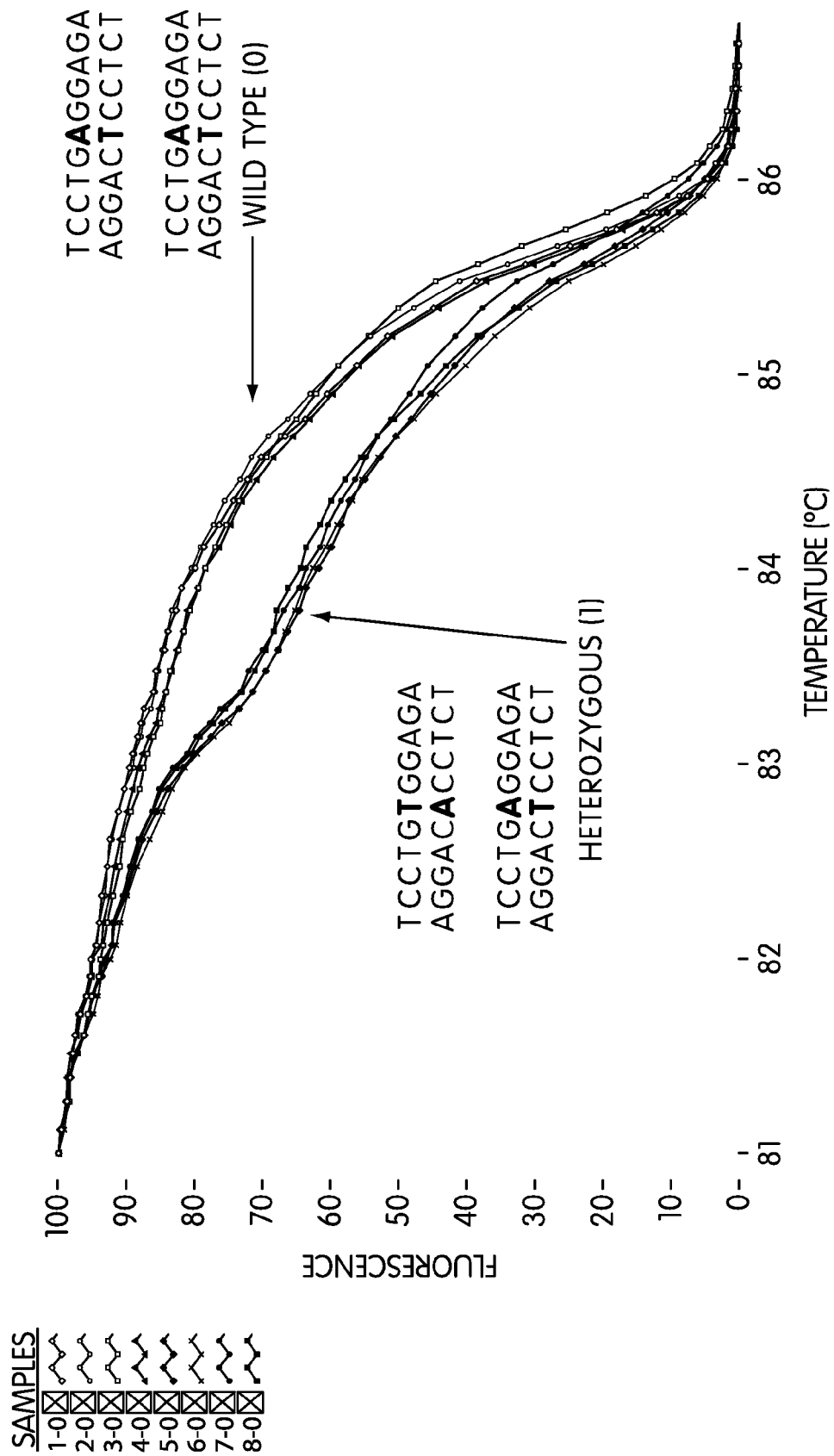
FIG. 3 is a fluorescence vs temperature plot showing curves of multiple assays and showing heterozygous and wild type curves in which the wild type curve is shown with two copies of SEQ ID NO:1 and its complementary strand SEQ ID NO:2, while the heterozygous curve is shown with one copy of SEQ ID NO:1 and its complementary strand SEQ ID NO:2 and the second copy of the gene contains the substitution of T for A (SEQ ID NO:3) with its complementary sequence (SEQ ID NO:4)

FIG. 3 shows exemplary fluorescence vs temperature profiles for a single thermal melt SNP assay result for eight different samples. Comparison of the actual fluorescence vs temperature profile with a predetermined expected profile can indicate whether the result is "wild type" (i.e., normal) or heterozygous (i.e., abnormal). There are many features of the fluorescence vs temperature curve that can be used for the comparison. In the illustrated example, the temperature at which the fluorescence drops to a predetermined level is used. For example, in the illustrated embodiment, the temperature at which the fluorescence drops to 70% may be compared. The four upper curves exhibit characteristics predetermined to be normal, with the fluorescence dropping to 70% at around 84.7° C., thereby indicating a wild type, and the four lower curves exhibit characteristics other than the predetermined normal, with the fluorescence dropping to 70% at around 83.6° C., thereby indicating heterozygotes. Other characteristic features of the curve can be used for the comparison, such as slope, shape or smoothness of the curve, area under the curve, etc. The SNP test result is then converted to a digital signal, by, for example, designating the heterozygote genotype as a "1" and the wild type as a "0". Alternatively, the heterozygote may be designated as a "0" and the wild type as a "1".

In other applications, the method of the present invention may be used to detect DNA sequence variations of interest other than SNPs. Examples of DNA sequence variations include, but are not limited to, insertions, deletions, point mutations and rearrangements. In addition, appropriate melt curves can be selected to distinguish between wild-type and homozygosity of DNA sequence variations, as well as between wild-type, heterozygosity of the DNA sequence variations and homozygosity of DNA sequence variations.

FIG. 4 shows an exemplary digital output from eight SNP multiplex assays (A-H) performed on thirty patient DNA samples and two control DNA samples. Each of the eight PCR reactions and thermal melts is performed twice. Each column represents the results of a single SNP assay that was performed on each of the thirty patient samples and two controls, and each row represents the results of all the SNP assays (A-H), each performed twice, for a single patient or control.

To increase the confidence in the observed result of any given SNP assay for a particular patient sample, the same SNP assay can be performed two or more times, with each additional performance of the assay increasing the confidence in the observed result. To increase the confidence in a diagnosis or therapy response prediction, where multiple SNPs may be relevant to the particular diagnosis or prediction, two or more relevant SNP tests can be performed on the patient sample. It may not be necessary, however, to analyze all the possible SNPs that are relevant to a particular diagnosis or prediction, if sufficient confidence of the diagnosis or prediction can be achieved with less than all SNPs.

In one embodiment, the invention optionally comprises statistical or probabilistic system software that performs one or more statistical or probabilistic analysis of assay results received from one or more of the tests to derive a confidence level for a diagnosis or prediction. For example, the statistical or probabilistic analysis can include Poisson analysis, Monte Carlo analysis, application of a genetic algorithm, neural network training, Markov modeling, hidden Markov modeling, multidimensional scaling, partial least square (PLS) analysis, and/or principle component analysis (PCA). The statistical or probabilistic analysis optionally comprises quantitatively determining a confidence level for a diagnosis or prediction.

General references that are useful in understanding how to generate and analyze data, as well as other relevant concepts include: Weiss (*Introductory Statistics*, 7th Ed., Addison-Wesley, Reading, Mass., 2004); Weiss (*Elementary Statistics*, 5th Ed., Addison-Wesley, Reading, Mass., 2001); Berinstein (*Finding Statistics Online: How to Locate the Elusive Numbers You Need*, Information Today, Medford, N.J., 1998); Everitt, (*The Cambridge Dictionary of Statistics*, Cambridge University Press, New York, 1998); Kotz (*Encyclopedia of Statistical Sciences*, vol. 1-9 plus supplements, Wiley, New York, 1988); Dillon and Goldstein (*Multivariate Analysis: Methods and Applications*, Wiley, N.Y., 1984); Tabachnick and Fidell (*Using Multivariate Statistics*, HarperCollins College Publishers, New York, 1996); Box et al. (*Statistics for Experimenters*, Wiley, N.Y., 1978); Cornell (*Experiments with Mixtures*, Wiley, N.Y., 1990); John (*Statistical Design and Analysis of Experiments*, SIAM, Philadelphia, 1998); Gibas and Jambeck (*Bioinformatics Computer Skills*, O'Reilly, Sebastipol, Calif., 2001); Pevzner (*Computational Molecular Biology and Algorithmic Approach*, The MIT Press, Cambridge, Mass., 2000); Durbin et al. (*Biological Sequence Analysis: Probabilistic Models of Proteins and Nucleic Acids*, Cambridge University Press, Cambridge, UK, 1998); and Rashidi and Buehler (*Bioinformatic Basics: Applications in Biological Science and Medicine*, CRC Press LLC, Boca Raton, Fla., 2000). The disclosure of each of these references is incorporated by reference herein.

The statistical functions noted above can also be incorporated into system software, e.g., embodied in the main control and processing computer 105 or in the post PCR analyzer 116, in computer memory or on computer readable media.

By way of example, assume, for a particular disease, there are ten known SNPs relevant to making a diagnosis of the particular genetic predisposition or carrier state (for example, a disease or risk of developing the disease). A diagnosis of a patient sample may begin by running five of the ten relevant SNPs on the patient sample. The result of each SNP test is a 1 (heterozygote) or 0 (wild type). Each SNP test can be run multiple times to instill a level of confidence that the result observed, 1 or 0, is accurate. If, at the conclusion of the five SNP tests, all five indicate that the patient does or does not carry the disease, or risk of carrying the disease, one could have a reasonable level of confidence in the diagnosis, and further tests may be unnecessary. On the other hand, if two SNP tests indicate that the patient does or does not carry the disease and three indicate the opposite, there may be little basis for a high level of confidence in the ultimate diagnosis, and further SNP tests (up to five more are still available) may be warranted.

In accordance with the present invention, performing multiple, different SNP tests and performing each SNP test multiple times is easily facilitated in a continuous flow of patient sample material through a microfluidic channel, wherein, for each SNP test to be performed, an amount of the appropriate assay-specific reagents is sipped into the channel. Where additional SNP tests are desired to increase the level of confidence in a diagnosis or prediction (whether additional, different SNP tests are desired or already-performed SNP tests need to be repeated), this can be determined and effected real-time in accordance with the invention. The SNP test results are simple and digital, i.e., 1 or 0, and the implications of the test results with respect to the diagnosis or prediction are known. Thus, if, after a number of test results are observed, it is determined that additional tests are needed, additional assay-specific reagents corresponding to the tests to be repeated or the additional, different tests to be performed, can be introduced in the continuous flow of patient sample through the microfluidic channel.

Figure 5:
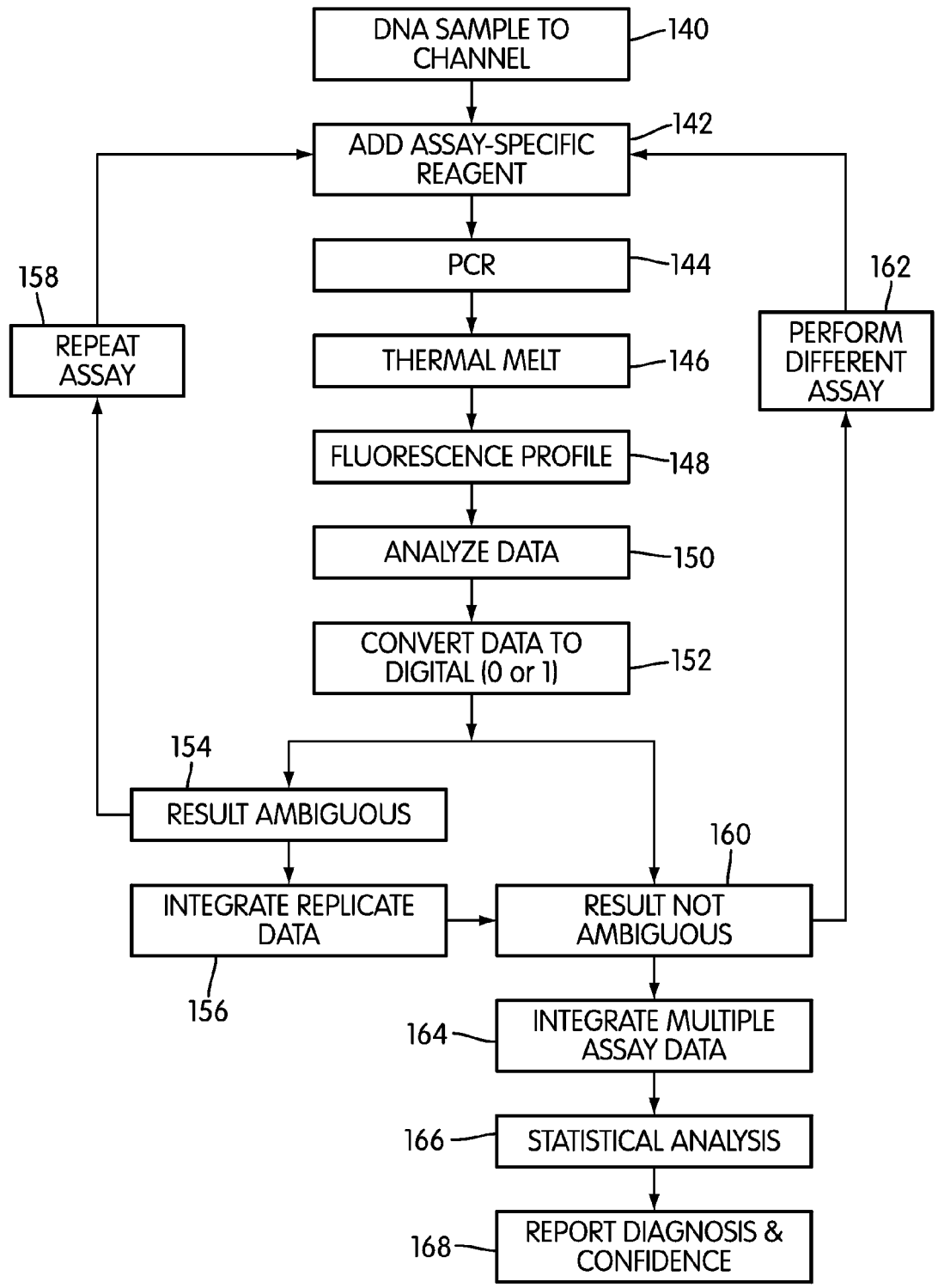
FIG. 5 is a flow chart illustrating a process embodying aspects of the present invention for making a diagnosis or a prediction using continuous, multiplex digital assays.

A flow chart illustrating a process for making a diagnosis with respect to a disease, risk of developing a disease or for making a prediction regarding a therapeutic drug treatment in accordance with aspects of the present invention is shown in FIG. 5. In Step 140, sample material—preferably genomic DNA material—is provided to a reaction channel. For example, the sample material can be provided to sample wells 122 of the microfluidic chip 120 so that the sample material will flow into the channel 103 upon application of a vacuum to the channel 103. In Step 142, assay-specific reagents are added to sample material within the channel 103, for example, by alternately sipping the reagents and buffer fluid through sipper 126 to be distributed into the channels 103, as described above.

In Step 144, a PCR procedure is performed on the reagent/sample mixture, i.e., on the reagent set 132 as the reagent set progresses down the channel 103, as described above. In Step 146, a thermal melt procedure is performed on the sample as the sample progresses down the channel 103. A fluorescence vs temperature profile is obtained on the sample material in Step 150, and, in Step 152, the fluorescence profile data is analyzed to obtain a digital result (1 or 0) as to the presence of the SNP of interest. If the test results are ambiguous (Step 154) obtaining more test results by repeating the same assay (Step 158) one or more times may increase the confidence in the test result. The replicate test data is integrated in Step 156, for example, by any appropriate statistical analysis technique known to persons of ordinary skill in the art, to achieve a result that is not ambiguous.

Where a test result is not ambiguous, Step 160, additional, different assays may be performed on the sample (Step 162) to get more "data points" relevant to the diagnosis or prediction. Each different assay may be performed more than once (Steps 154, 156, 158) to achieve an unambiguous result with respect to each assay performed on the sample. The additional test data is integrated in Step 164, for example, by any appropriate statistical analysis technique known to persons of ordinary skill in the art (Step 166), and the resulting diagnosis or prediction is reported with a level of confidence in Step 168 (e.g., "the tests indicate with a confidence level of 95% that patient Jones is a carrier of disease X").

The system for performing the process of FIG. 5 is preferably automated and computer-controlled, and the data generated by the system is a continuous stream of bits identifying the result for each PCR reaction.

Certain aspects and exemplary embodiments described herein disclose monitoring the thermal melt process using fluorescence. The present invention is not limited to these aspects and exemplary embodiments. In other aspects, thermal melting can be monitored by other means that detect the dissociation of double-stranded DNA, such as, for example, by UV absorbance or the use of non-fluorescent reporter dyes or molecules.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for performing digital multiplex PCR assay within a plurality of reaction channels of a microfluidic chip to identify DNA sequence variations in each of a plurality of patient samples to diagnose a disease status, a disease risk or predict a therapeutic drug response for each patient, said method comprising:

(A) for each patient sample, providing a flow of genomic DNA sample within one of the reaction channels, each reaction channel having a different patient sample;

(B) introducing a plurality of different assay-specific reagent solutions to the flow of genomic DNA sample in a reaction channel to form a plurality of test mixtures and simultaneously perform different assays on the test mixtures in the reaction channel, wherein each of the plurality of the test mixtures in the reaction channel undergoes a different assay;

(C) performing a PCR procedure on the test mixture within the reaction channel;

(D) performing a thermal melt procedure on the test mixture after performing the PCR procedure;

(E) collecting data on the thermal melt procedure;

(F) performing an analysis of the collected thermal melt data with a controller programmed to ascertain the presence or absence of a DNA sequence variation of interest within the test mixture;

(G) performing a conversion of the results of the analyzing step with the controller into a digital signal by designat-
ing a result indicating the presence of the DNA sequence variation of interest as 1 and designating a result indicating the absence of the DNA sequence variation of interest as 0, or vice versa;

(H) performing an analysis of the outcome of step G with the controller for each of the patient samples to determine whether the outcome is ambiguous, such that if the controller determines that the outcome is ambiguous, the controller causes the repeating of steps B through G at least once with the same assay-specific reagent solutions used in step B to improve the confidence in the determination of the presence or absence of the DNA sequence variation of interest;

(I) performing an analysis of the outcome of step G with the controller for each of the patient samples to determine whether the outcome is ambiguous, such that if the controller determines that the outcome is not ambiguous, the controller causes the repeating of steps B through H at least one time with a different assay-specific reagent solution adapted to identify a different DNA sequence variation relevant to the diagnosis or prediction; and (J) performing a statistical analysis on the results of steps B through I with the controller to derive a diagnosis or a prediction and a level of confidence in the diagnosis or prediction.

2. The method of claim 1, wherein step B comprises alternately introducing an amount of reagent material and buffer material into each of the reaction channels to form, along the length of each reaction channel, a continuous flow comprising boluses of test solution sequentially alternating with carrier fluid, wherein the test solution comprises a mixture of sample and reagent material, and the carrier fluid comprises a mixture of sample and buffer material.

3. The method of claim 2, wherein the collecting data on the thermal melt procedure step comprises collecting fluorescence profile data from the test mixture while performing the thermal melt procedure.

4. The method of claim 3, wherein step D comprises ramping up the temperature of the bolus of test mixture and step E comprises generating a signal strength versus temperature correlation.

5. The method of claim 4, wherein step F comprises comparing the correlation to a predetermined expected correlation and assessing a result from the deviation of the correlation from the expected correlation.

6. The method of claim 5, wherein generating a signal strength versus temperature correlation comprises plotting a fluorescence vs temperature curve for each bolus of test mixture, and the comparing step comprises comparing the shape of each fluorescence vs temperature curve with an expected shape of the fluorescence vs temperature curve.

7. The method of claim 5, wherein generating a signal strength versus temperature correlation comprises plotting a fluorescence vs temperature curve for each bolus of test mixture, and the comparing step comprises comparing the temperature at which the fluorescence drops to a predetermined level with an expected temperature at which the fluorescence drops to the predetermined level.

8. The method of claim 3, wherein the fluorescence profile comprises the fluorescence emitted by the bolus of test mixture.

9. The method of claim 1, wherein the microfluidic chip comprises:
a sample well and a waste well on opposite ends of each reaction channel; a sipper; and
a network of channels emanating from the sipper and connecting the sipper to each of said plurality of reaction channels and configured to divide substance drawn by the sipper among each of the reaction channels.

10. The method of claim 1, wherein the confidence level is a function of the number of different assays performed.

11. The method of claim 1, wherein the confidence level is a function of the number of times each assay is repeated.

12. The method of claim 1, wherein the ascertaining the presence or absence of DNA sequence variation includes ascertaining the presence or absence of single nucleotide polymorphisms.

13. A method for performing multiple assays on multiple samples with a fluid chip comprising a plurality of reaction channels, said method comprising:
providing a continuous flow of sample within each of the reaction channels, each reaction channel having a different patient sample;
alternately introducing an amount of reagent material and buffer material into each of the reaction channels to form, along the length of each reaction channel, a continuous flow comprising boluses of test solution sequentially alternating with carrier fluid, wherein the test solution for each bolus comprises a mixture of sample and assay-specific reagent material to simultaneously perform different assays on the boluses within a reaction channel, wherein each bolus in the reaction channel undergoes a different assay, and the carrier fluid comprises a mixture of sample and buffer material;
performing an amplification procedure on the test solution within the continuous flow within each reaction channel;
performing a thermal melt procedure on the amplified test solution within each reaction channel;
detecting a signal emitted by each bolus of test solution during the thermal melt procedure; and
performing an analysis of the detected signal with a controller to ascertain the presence or absence of a nucleotide of interest within the bolus of test solution.

14. The method of claim 13, wherein the detecting step comprises generating a signal strength versus temperature correlation.

15. he method of claim 14, wherein the detecting step further comprises comparing the generated correlation to a predetermined expected correlation and assessing a result from a deviation of the generated correlation from the expected correlation.

16. The method of claim 15, wherein the detected signal is the fluorescence emitted by the bolus of test solution.

17. The method of claim 16, wherein generating a signal strength versus temperature correlation comprises plotting a fluorescence vs temperature curve for each bolus of test solution, and the comparing step comprises comparing the shape of each fluorescence vs temperature curve with an expected shape of the fluorescence vs temperature curve.

18. The method of claim 16, wherein generating a signal strength versus temperature correlation comprises plotting a fluorescence vs temperature curve for each bolus of test solution, and the comparing step comprises comparing the temperature at which the fluorescence drops to a predetermined level with an expected temperature at which the fluorescence drops to the predetermined level.

19. The method of claim 13, wherein the nucleotide of interest is a single nucleotide polymorphism.

20. The method of claim 13, wherein the fluid chip is a microfluidic chip comprising:
a sample well and a waste well on opposite ends of each reaction channel;
a sipper; and
a network of channels emanating from the sipper and connecting the sipper to each of said plurality of reaction channels and configured to divide substance drawn by the sipper among each of the reaction channels.

21. The method of claim 13, wherein the reagent material and the buffer material are introduced into each of the reaction channels through a sipper.

22. A system for performing digital, multiplex PCR assays comprising:
a microfluidic chip comprising: a plurality of reaction channels;
a sample well and a waste well on opposite ends of each reaction channel;
a sipper; and
a network of channels emanating from the sipper and connecting the sipper to each of said plurality of reaction channels and configured to divide substance drawn by the sipper among each of the reaction channels;
a temperature control system integral with or proximal to the microfluidic chip and configured to thermocycle the contents along a defined section of each reaction channel and to perform a thermal melt of the contents;
an optical imaging system integral with or proximal to the microfluidic chip and configured to illuminate each reaction channel and to detect a fluorescent signal emitted by the contents of each reaction channel at a plurality of locations along each reaction channel; and a controller programmed to cause the system to:
generate a continuous flow of sample material within each reaction channel;
alternately introduce an amount of reagent material and buffer material through the sipper into each of the reaction channels to form, along the length of each reaction channel, a continuous flow comprising boluses of test solution sequentially alternating with carrier fluid, wherein the test solution for each bolus comprises a mixture of sample and different assay-specific reagent material to simultaneously perform different assays within a reaction channel, wherein each bolus in the reaction channel undergoes a different assay, and the carrier fluid comprises a mixture of sample and buffer material;
thermocyle the contents of each reaction channel with the temperature control system to perform an amplification procedure on the test solution within the continuous flow within each reaction channel;
perform a thermal melt on the test solution with the temperature control system;
after performing the thermal melt procedure, detect a signal emitted by each bolus of test solution with the optical imaging system; and
analyze the detected signal to ascertain the presence or absence of a nucleotide of interest within the bolus of test solution.

23. The system of claim 22, wherein the controller is configured to cause the temperature control system to ramp up the temperature of the bolus of test solution.

24. The system of claim 23, wherein the controller is programmed to compare the correlation to a predetermined expected correlation and assessing a result from the deviation of the correlation from the expected correlation.

25. A method for performing digital multiplex PCR assay within a plurality of reaction channels of a microfluidic chip to identify DNA sequence variations in each of a plurality of patient samples to diagnose a disease status, a disease risk or predict a therapeutic drug response for each patient, said method comprising:
  (A) for each patient sample, providing a flow of genomic DNA sample within one of the reaction channels, each reaction channel having a different patient sample;
  (B) introducing a plurality of assay-specific reagent solutions to the flow of genomic DNA sample in a reaction channel to form a plurality of test mixtures and simultaneously perform different assays on the test mixtures in the reaction channel, wherein each of the plurality of the test mixtures within the reaction channel undergoes a different assay;
  (C) performing a PCR procedure on the test mixture within the reaction channel;
  (D) performing a thermal melt procedure on the test mixture after performing the PCR procedure;
  (E) collecting data on the thermal melt procedure;
  (F) performing an analysis of the collected thermal melt data with a controller to ascertain the presence or absence of a DNA sequence variation of interest within the test mixture; and
  (G) performing a conversion of the results of the analyzing step with a controller to a digital signal by designating a result indicating the presence of the DNA sequence variation of interest as 1 and designating a result indicating the absence of the DNA sequence variation of interest as 0, or vice versa;
  (H) performing an analysis of the outcome of step G for each of the patient samples with the controller to determine whether the result is collectively ambiguous,
  (I) causing the performing of one or both of the following steps by the controller based on the result of the analysis in step H:
    i) repeating steps B through H at least once with the same assay-specific reagent solution to improve the confidence in the determination of the presence or absence of the DNA sequence variation of interest;
    ii) repeating steps B through H at least one time with a different assay-specific reagent solution adapted to identify a different DNA sequence variation relevant to the diagnosis or prediction;
  (J) performing a statistical analysis on the results of steps B through I to derive a diagnosis or a prediction and a level of confidence in the diagnosis or prediction and a level of confidence in the diagnosis or prediction.

26. A method for performing digital multiplex PCR assay within a plurality of reaction channels of a microfluidic chip to identify DNA sequence variations in each of a plurality of patient samples to diagnose a disease status, a disease risk or predict a therapeutic drug response for each patient, said method comprising:
  (A) for each patient sample, providing a flow of genomic DNA sample within one of the reaction channels, wherein the patient samples are run in parallel across the plurality of reaction channels, each reaction channel having a different patient sample;
  (B) introducing a plurality of assay-specific reagent solutions to the flow of genomic DNA sample in a reaction channel to form a plurality of test mixtures and simultaneously perform different assays on the test mixtures in the reaction channel, wherein each of the plurality of the test mixtures within the reaction channel undergoes a different assay;
  (C) performing a PCR procedure on the test mixture within the reaction channel;
  (D) performing a thermal melt procedure on the test mixture after performing the PCR procedure;
  (E) collecting data on the thermal melt procedure; and
  performing an analysis of the collected thermal melt data with a controller programmed to ascertain the presence or absence of a DNA sequence variation of interest within the test mixture.

* * * * *